(12) United States Patent
Lu

(10) Patent No.: US 8,393,233 B2
(45) Date of Patent: Mar. 12, 2013

(54) FORCE METER

(76) Inventor: Guixian Lu, Pontiac, MI (US)

( * ) Notice: Subject to any disclaimer, the term of this patent is extended or adjusted under 35 U.S.C. 154(b) by 541 days.

(21) Appl. No.: 12/798,240

(22) Filed: Apr. 1, 2010

(65) Prior Publication Data

US 2011/0245706 A1    Oct. 6, 2011

Related U.S. Application Data

(63) Continuation-in-part of application No. 11/546,851, filed on Oct. 13, 2006, now Pat. No. 7,611,472.

(51) Int. Cl.
*G01F 1/42* (2006.01)
*A61B 5/08* (2006.01)
(52) U.S. Cl. .................... 73/862.61; 600/539
(58) Field of Classification Search ........... 73/862.61; 600/539
See application file for complete search history.

(56) References Cited

U.S. PATENT DOCUMENTS

| 4,628,744 A * | 12/1986 | Lew | 73/861.355 |
| 7,611,472 B2 * | 11/2009 | Lu | 600/538 |
| 2012/0071778 A1 * | 3/2012 | Wang | 600/539 |

* cited by examiner

*Primary Examiner* — Lisa Caputo
*Assistant Examiner* — Jamel Williams

(57) ABSTRACT

The primary application of this force meter is measurement of fluid flow. A force on the force sensor push the force sensor away from the original position. The deviation of the force sensor is detected by a proximity sensor. An electronic unit takes the position signal from the proximity sensor as a feedback. The electronic unit generates electric current to an electromagnetic anti-torque means. The electromagnetic anti-torque means generates an anti-torque on force sensor to prevent the force sensor from moving away from the original position. A display unit measures the electric current and calculates velocity and rate of fluid before displays the results.

9 Claims, 4 Drawing Sheets

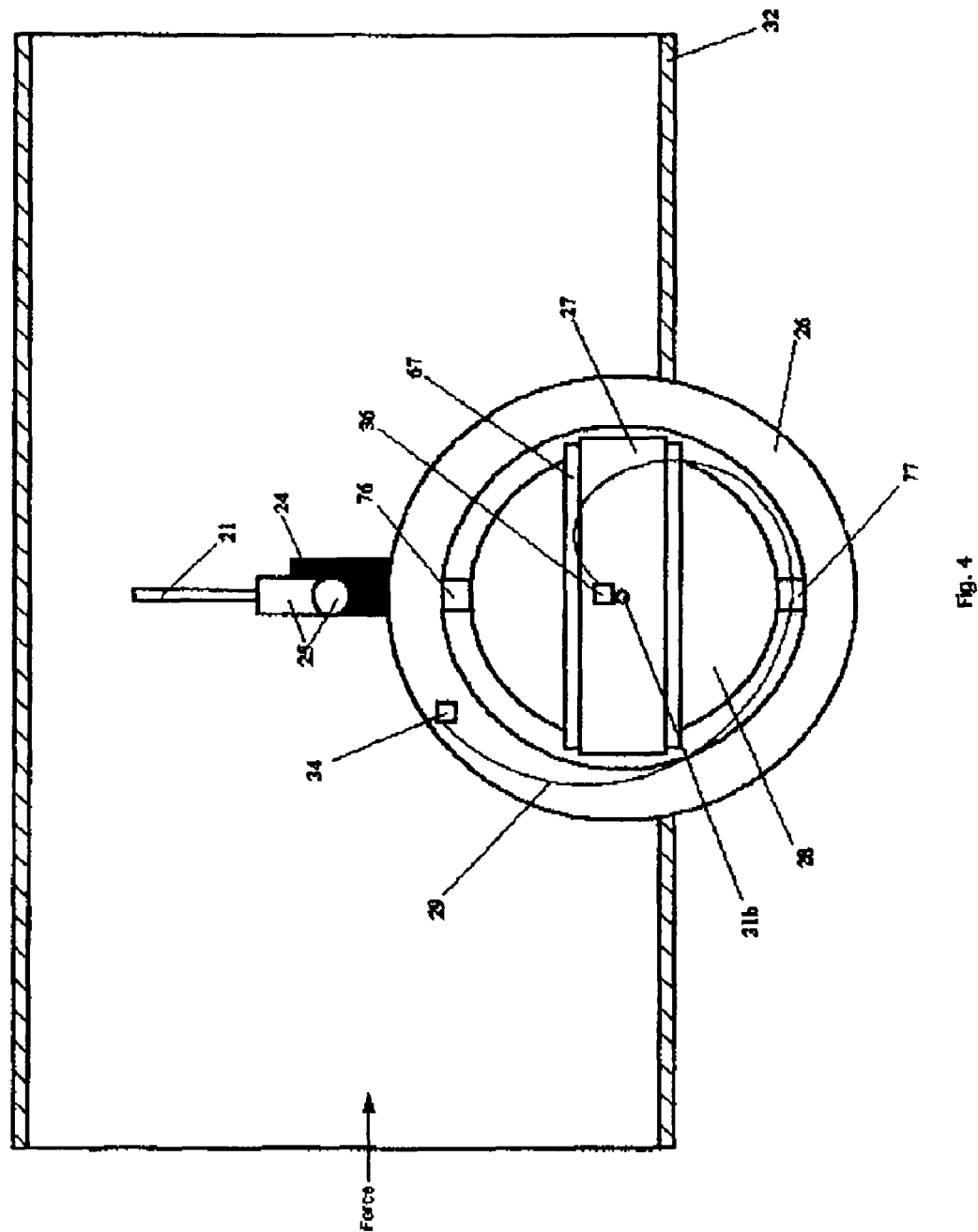

FORCE METER

CROSS REFERENCE TO RELATED APPLICATION

This application is a continuation-in-part of U.S. application Ser. No. 11/546,851, filed Oct. 13, 2006, now U.S. Pat. No. 7,611,472

BACKGROUND OF THE INVENTION

A flow meter using turbine is not as accurate to low velocity flow due to large inertia of the turbine and significant friction at the axle of the turbine. It is not as accurate to high velocity either because turbine adds too much resistance to flow.

A target flow meter and a differential pressure flow meter is not as accurate, especially flow is slow, because signal deviations either generated by the strain sensors or generated in the amplifiers are amplified.

The present invention measures force such as force generated by fluid flow on a force sensor. It can be used to measure breathing of patients. It can be used to measure velocity and rate of gas and liquid in industries. The present invention costs less to manufacture due to simplicity. It is very accurate. It adds less resistance to fluid flow.

The present invention can be bi-directional.

SUMMARY OF THE INVENTION

The present invention directly measures breathing airflow instead of measuring the resistance of the chest. The objective of the present invention is to increase sensitivity of apnea monitor. Another objective is to measure vital capacity. The present invention collects parameters about breathing. Based on the parameters, vital capacity can be calculated. The parameters will also help in diagnoses.

DESCRIPTION OF DRAWINGS

FIG. 1 is a cut-half view of a force meter. Item 1 is a force sensor. Item 2, secured to axle 11, is a support for force sensor 1. Item 3, secured to case 14, is a light source, such as emitting diodes. Item 4 is a light controller secured to axle 11. Item 5, secured to case 14, is a light sensor, such as photo diodes sending position signal to electronic unit 15. Items 3, 4, and 5 form a optical proximity sensor. Item 6, secured to axle 11, is a piece of movable magnet with S pole up. Item 7, secured to case 14, is a fixed coil. Item 8, secured to axle 11, is a movable magnet with N pole up. The lower portion of movable magnet 6 is inside of fixed coil 7. Two wire ends (not showed) of fixed coil 7 are electrically connected to electronic unit 15. Item 9 is a reset magnet to rotate force sensor 1 to the original position when there is no external force. Reset magnet 9 secured to case 14 through an adjustable knob 16. Item 10 and item 12 are bearings. Item 15 is electronic unit such as micro-controller that amplifies position signal from light source 5 to electric current going through coil 7. Item 20 is the central line of axle 11. Item 13 is a balance weight to make central weight of the assembly at or near the central line 20. The assembly consists of items 1, 2, 11, 13, 4, 6, and 8. Item 50 is a display unit that convert value the electric current to force before displaying.

FIG. 2 is a side view of the first embodiment. The items 14, 8, 9, 15, 16, and 50 are removed. Fixed coil 7 is cut-half.

FIG. 3 and FIG. 4 show the second embodiment. In FIG. 3, item 32, 26, 80, and 81 are cut-half. Item 80 and 81 are bearings. Item 21 is a force sensor. Item 21 is secured to axle 31a through support 22. Item 23, secured to the case 32, is a light source. Item 24, secured to axle 31a, is a light controller. Item 25, secured to the case 32, is a light sensor. Light source 23, light controller 24, and light sensor 25 form an optical proximity sensor. Light sensor 25 is electrically connected to input lines (not shown) of electronic unit 78. Light sensor 25 sends position signal to electronic unit 78. Item 26, secured to the case 32, is a fixed magnet of ring shape. Fixed magnet 28 is secured to fixed magnet 26 through supports 76 and 77. Fixed magnet 28 and fixed magnet 26 generate magnetic field between them. Item 27 is a movable coil winded on frame 67. Frame 67 is rotatable in the gap between fixed magnet 28 and fixed magnet 26. Frame 67 is supported by axle 31a and axle 31b. Axle 31a and axle 31b have the same central line 90 so that they are considered as one axle. Item 78 is electronic unit such as micro-controller that amplifies the position signal from light sensor 25 to electric current going to movable coil 27 through reset gossamer 29 and reset gossamer 30. Item 36 is the first end of reset gossamer 29. Item 34 is the second end of reset gossamer 29. Item 37 is the first end of reset gossamer 30. Item 35 is the second end of reset gossamer 30. Item 41 is the first end of movable coil 27. Item 42 is the second end of movable coil 27. Item 36 is electrically connected to item 41. Item 34 is electrically connected to first output line 101 of electronic unit 78. Item 37 is electrically connected to item 42. Item 35 is electrically connected to second output line 102 of electronic unit 78. Item 36 is mechanically secured to axle 31b. Item 34 is mechanically secured to case 32. Item 37 is mechanically secured to axle 31a. Item 35 is mechanically secured to case 32. Item 33 is a balance weight that makes central weight of an assembly at or near central line 90 of axle 31a and axle 31b. The assembly consists of force sensor 21, support 22, axle 31a, balance 33, light controller 24, frame 67, movable coil 27, and axle 31b. Item 100 is a display unit that converts value of the electric current to value of force before displaying.

FIG. 4 is a side view of the second embodiment. Force sensor 21 is at the original position. A portion of case 32 is removed. Bearing 81 and electronic unit 78 are removed.

DETAILED DESCRIPTION

External force of fluid flow acting on the force sensor can be expressed as $$F = cd\,v^2\,At/2$$

where
F=external force (N)
c=overall force sensor coefficient obtained from empirical data
d=density of fluid (kg/m3)
v=fluid velocity (m/s)
At=area of force sensor (square m)

When there is an external force to the force sensor, the force sensor is moved away from the original position. A proximity sensor measures the position deviation and generates a position signal. The proximity sensor can be optical, capacitive, inductive, and more. The position signal is amplified to electric current by an electronic unit The electric current drives an electromagnet means of anti-force to generate an anti-force. The anti-force acts on the force sensor to prevent the force sensor from moving away from the original position. When the torque made by the electromagnet means of anti-force is equal to the torque made by the external force, the force sensor stops moving. The position deviation, the position signal, the electric current, and the anti-force form a closed loop system of negative feedback. A display unit measures the electric current and converts the value of electric current to value of force. The position deviation, the position signal, the electric current, and the anti-force form a closed loop of negative feedback.

Figure 1:
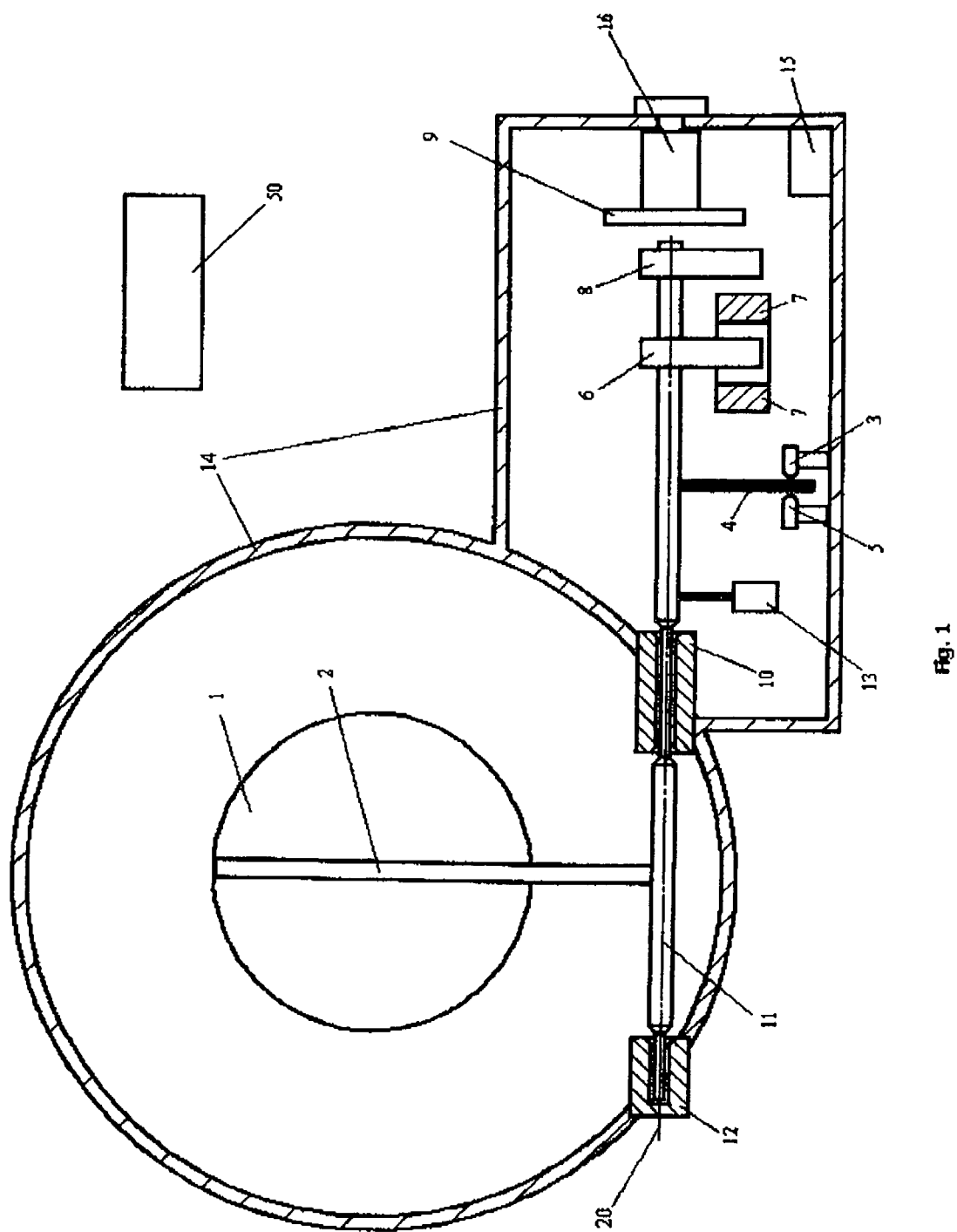
FIG. 1 and FIG. 2 show the first embodiment.
Figure 2:
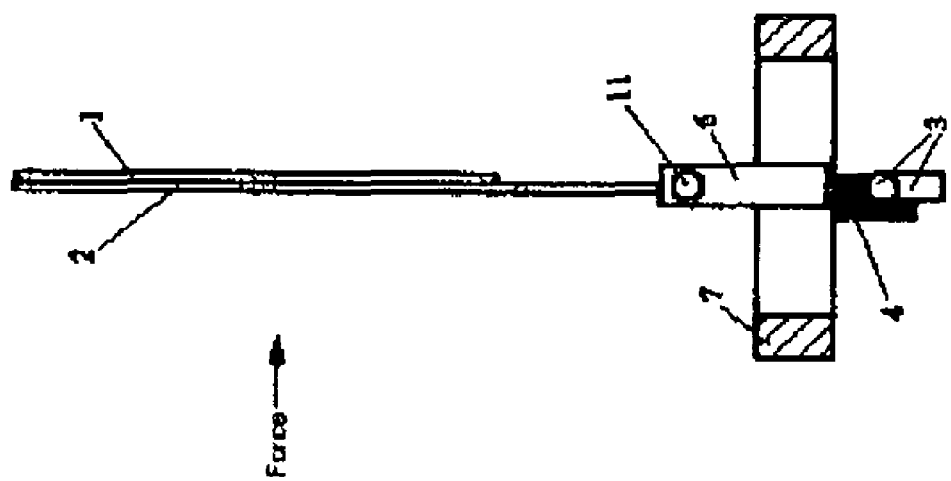

FIG. 1 and FIG. 2 show the first embodiment. When there is no external force, the force sensor is in the original position (see FIG. 2) and the light controller blocks the light path from light source 3 to the light sensor 5. The output from the light sensor 5 is zero. When an external force rotates force sensor 1 clockwise around the axle 11, the force sensor 1 deviates from the original position. The optical proximity sensor is consists of light source 3, light controller 4, and light sensor 5. When the force sensor is rotates, it bring the light controller 4 to move away from between the light source 3 and light sensor 5. When the light controller rotates, it changes light energy rate from light source 3 to light sensor 5 (see FIG. 1). Change of light energy rate causes change of position signal from the light sensor 5. The more position deviation is the stronger the position signal is. The position signal is amplified to electric current by the electronic unit 15. The stronger the position signal is the stronger the electric current is. The electromagnet means of anti-force consists of fixed coil 7, movable magnet 6, and movable magnet 8. The electric current goes through fixed coil 7. Interaction of the electric current with movable magnets 6 and 8 generates an anti-force to rotate the force sensor 1 backwards to the original position. The stronger the electric current is the stronger the anti-force is. If the gain of the amplifier in the electronic unit is high enough, the anti-torque made by the anti-force increases faster than the torque made by the external force. When the anti-torque is equal to the torque made by the external force, force sensor stops rotation. The display unit 50 measures value of the electric current. With value of electric current, anti-force can be calculated. The external force can be determined. The velocity of fluid can be calculated by the above formula. Rate of fluid can be calculated by integrating velocity over a unit of time. A proportional-integral-derivative controller may be used in the electronic unit to improve the system dynamics.

Figure 3:
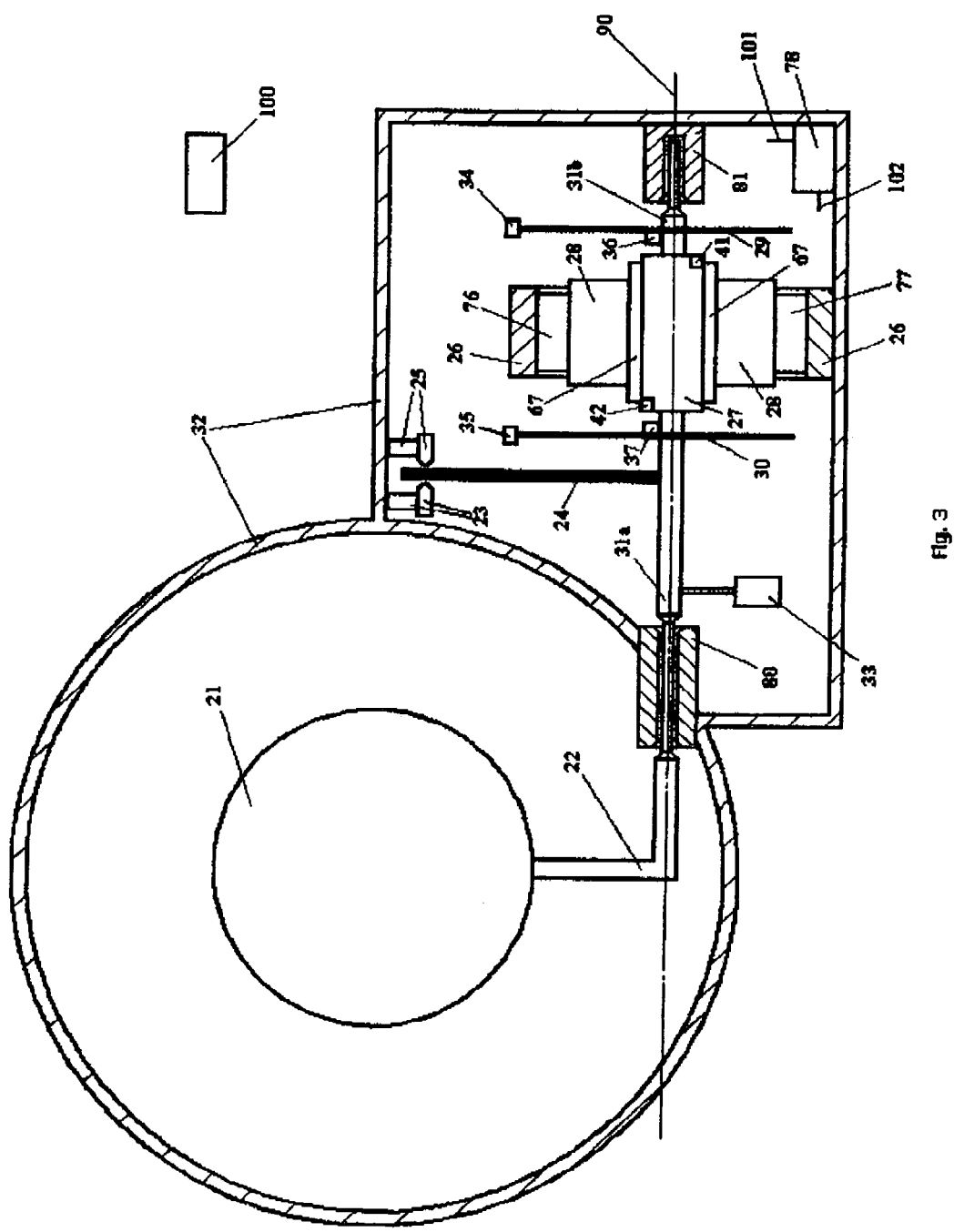

FIG. 3 and FIG. 4 show the second embodiment. The original position of force sensor 21 can be seen in FIG. 4. When there is no external force, the light controller 24 blocks light from light source 23 to light sensor 25. When external force rotates force sensor 21 clockwise, light from light source 23 goes to light sensor 25. Position signal from light sensor 25 is amplified to electric current by electronic unit 78. Electric current is sent to movable coil 27 through gossamer 29 and gossamer 30. An anti-force is generated by interaction of electric current in movable coil 27 with magnetic field from fixed magnet 26 and fixed magnet 28. Anti-torque made by the anti-force rotates the force sensor 21 backwards to original position. When anti-torque made by anti-f is equal the torque made by external force, rotation of force sensor 21 stops. The electric current is measured by display unit 100. Value of electric current is converted to value of velocity or rate of fluid before displayed.

What is claimed is:

1. A force meter for measuring external force comprising:
    A) A case;
    B) A force sensor, said force sensor moves away from an original position when an external force is applied to said force sensor;
    C) A proximity sensor, said proximity sensor measures a position deviation of said force sensor from said original position, said proximity sensor generates a position signal when a position deviation is detected, the larger said position deviation is the stronger said position signal is;
    D) An electromagnetic means of anti-force, said electromagnetic means of anti-force generates an anti-force to move said force sensor backwards to said original position while receiving an electric current, the stronger said electric current is the stronger said anti-force is;
    E) An electronic unit, said electronic unit generates said electric current while receiving said position signal, the stronger said position signal is the stronger said electric current is;
    F) A display unit, said display unit measures value of said electric current, said display unit converts value of said electric current to value of force, or other value related to force before displaying.

2. A force meter in claim 1, wherein said position deviation, said position signal, said electrical current, and said anti-force form a closed loop system of negative feedback that is preventing increment of said position deviation, while an external force is increasing said position deviation.

3. A force meter in claim 1, wherein said proximity sensor comprises a optical proximity sensor.

4. A force meter in claim 3, wherein said optical proximity sensor comprises at least a light controller, at least a light source, and at least a light sensor, said light source and said light sensor are secured to said case, said light controller is secured to said force sensor, said light controller moves between said light source and said light sensor to change light energy rate from said light source to said light sensor when the position of said force sensor changes.

5. A force meter in claim 1, wherein said electronic unit comprises a proportional-integral-derivative controller.

6. A force meter in claim 1, wherein said electromagnetic means of anti-force comprises a magnetic reset structure, an axle, at least a balance weight, at least a movable magnetic, and at least a fixed coil, said movable magnetic, interacting with said electric current in said fixed coils, generate said anti-force, said balance weight makes the central weight of an assembly at or near the central line of said axle, said movable magnetic are secured to said axle, said fixed coils are electrically connected to said electronic unit so that said electric current can go through said fixed coils, said fixed coils are secured to said case, said assembly comprises said movable magnetic, said force sensor, said axle, said balance weight, and said light controller.

7. A force meter in claim 6, wherein said magnetic reset structure comprises a reset magnet, said reset magnet is secured to said case, said reset magnet interacts with said movable magnetic to generate a torque rotating said force sensor to said original position when there is no external force.

8. A force meter in claim 1, wherein said electromagnetic means of anti-force comprises, at least a fixed magnet, a coil axle, a coil balance weight for making the central weight of a coil assembly at or near the central line of said coil axle, a movable coil, a means of electrical connection for said movable coil, said fixed magnets retract with said electric current in said movable coil to generate said anti-force, said fixed magnets are secured to said case, said movable coil is secured to said coil axle, said coil assembly comprises said movable coil, said force sensor, said coil axle, said coil balance weight, and said light controller.

9. A force meter in claim 8, wherein said means of electrical connection comprises at least two reset springs or two reset gossamer, said reset springs mechanically connect said coil assembly to said case to rotate said force sensor to said original position when there is no external force, said movable coil is electrically connected to said electronic unit through said two reset springs to receive said electric current.

* * * * *